United States Patent
Sugiyama et al.

(10) Patent No.: US 7,550,581 B2
(45) Date of Patent: Jun. 23, 2009

(54) GUANOSINE DERIVATIVES AND USE THEREOF

(75) Inventors: Hiroshi Sugiyama, Kyoto (JP); Yan Xu, Tokyo (JP); Reiko Ikeda, Saitama (JP)

(73) Assignee: Japan Science and Technology Agency, Saitama (JP)

( * ) Notice: Subject to any disclaimer, the term of this patent is extended or adjusted under 35 U.S.C. 154(b) by 41 days.

(21) Appl. No.: 10/546,107

(22) PCT Filed: Feb. 23, 2004

(86) PCT No.: PCT/JP2004/002068

§ 371 (c)(1),
(2), (4) Date: Aug. 18, 2005

(87) PCT Pub. No.: WO2004/076472

PCT Pub. Date: Sep. 10, 2004

(65) Prior Publication Data

US 2006/0235219 A1 Oct. 19, 2006

(30) Foreign Application Priority Data

Feb. 28, 2003 (JP) .............................. 2003-052817

(51) Int. Cl.
*C07H 21/00* (2006.01)
*C07H 19/04* (2006.01)
(52) U.S. Cl. ..................... 536/25.3; 536/26.7
(58) Field of Classification Search ................ 536/22.1, 536/25.3, 26.7
See application file for complete search history.

(56) References Cited

U.S. PATENT DOCUMENTS 4,415,732 A * 11/1983 Caruthers et al. .......... 536/26.5
5,292,873 A * 3/1994 Rokita et al. ............... 536/24.3

OTHER PUBLICATIONS

Uesugi et al., "Ribooligonucleotides, r(C-G-C-G) Analogues Containing 8-Substituted Guanosine Residues, Form Left Handed Duplexes with Z-Form-like Structure", Journal of the American Chemical Society, 1984, vol. 106, pp. 3675-3675.*
Sugiyama et al., "Synthesis, structure and thermodynamic properties of 8-methylguanine-containing oligonucleotides: Z-DNA under physiological salt conditions", Nucleic Acids Research, 1996, vol. 24, No. 7, pp. 1272-1278.*

Xu et al., "8-Methylguanosine: A Powerful Z-DNA Stabilizer", *J. Am. Chem. Soc.*, 125:13519-13524 (2003).
Oyoshi et al., "Efficient C2 α-Hydroxylation of Deoxyribose in Protein-induced Z-Form DNA", *J. Am. Chem. Soc.*, 125:1526-1531 (2003).
Kawai et al., "Conformation-Dependent Photochemistry of 5-Halouracil-Containing DNA: Stereospecific 2'α-Hydroxylation of Deoxyribose in Z-form DNA", *J. Am. Chem. Soc.*, 121:1391-1392 (1999).

* cited by examiner

*Primary Examiner*—Traviss C McIntosh, III
(74) *Attorney, Agent, or Firm*—Edwards Angell Palmer & Dodge LLP; Peter F. Corless; Dwight D. Kim

(57) ABSTRACT

It is intended to provide a novel monomer unit by which Z type DNA can be more effectively stabilized, a reagent for integrating this monomer unit into an oligonucleotide, and a method of stabilizing Z type DNA by using the reagent. Namely, a guanosine derivative represented by the following general formula [1]:

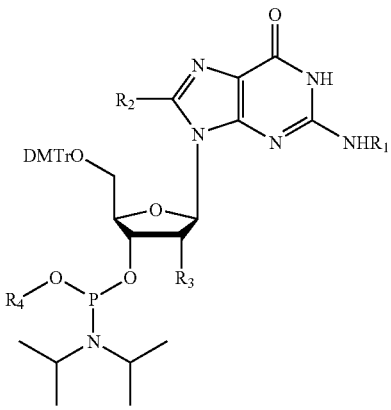

wherein $R^1$ represents acyl; $R^2$ represents lower alkyl; $R^3$ represents tri-substituted silyloxy or tetrahedropyranyloxy; and $R^4$ represents cyanoethyl or allyl; a reagent for stabilizing Z type DNA which contains the guanosine derivative; and a method of stabilizing Z type DNA by using the guanosine derivative. It is also intended to provide a method of transferring guanosine having lower alkyl at the 8-position into an oligonucleotide by using the guanosine derivative; and an oligonucleotide carrying guanosine having lower alkyl at the 8-position transferred thereinto.

2 Claims, 3 Drawing Sheets

GUANOSINE DERIVATIVES AND USE THEREOF

TECHNICAL FIELD

The present invention relates to novel guanosine derivatives useful as a reagent for stabilizing Z-form DNA, and a method for stabilizing Z-form DNA by using the protein.

BACKGROUND ART

Although Z-form DNA is a nucleotide found about 30 years ago, which has a left-handed Z form structure, biological roles of the Z-form DNA have not been well established. The reason is because it is difficult to obtain a stable left handed Z-form of nucleotide in a solution in the case of nucleotides used for studies, which usually have such a short length as 6 to 20 mers. Consequently, development of a monomer unit for stabilizing the Z-form DNA is demanded for studying the Z-form DNA.

The present inventors have previously found and reported in literatures that Z-form DNA can be stabilized by 8-methylguanosine (MeG) (e.g. refer to the prior art reference 1). They have also made numerous studies by using 8-methyldeoxyguanosine (e.g. refer to prior art references 1, 2, 3 and 4).

By using 8-methyldeoxyguanosine, stabilization of the Z-form DNA, which has been extremely difficult to obtain up to now, could be achieved to some extent. However, it is still insufficient to completely stabilize the Z-form DNA, and a further study to search a monomer unit to effectively stabilize the Z-form DNA is still demanded.

Prior art references relating to the present invention are as follows, and they are incorporated herein by reference.

1. Sugiyama, H.; Kawai, K.; Matsunaga, A.; Fujimoto, K.; Saito, I.; Robinson, H.; and Wang, A. H.-J., "Synthesis, Structure and Thermodynamic Properties of 8-Methylguanine-Containing Oligonucleotides Z-DNA under Physiological Salt Conditions."; Nucleic Acid Res., 1996, 24, 1272.
2. Kawai, K.; Saito, I.; Sugiyama, H., "Conformation Dependent Photochemistry of 5-Halouracil-Containing DNA: Stereospecific 2'-α-Hydroxylation of Deoxyribose in Z-form DNA."; J. Am. Chem. Soc. 1999, 121, 1391-1392.
3. Kawai, K.; Saito, I.; Kawashima, E.; Ishido, Y.; Sugiyama, H., "Intrastr and 2'-β-Hydrogen Abstraction of 5'-Adjacent Deoxy guanosine by Deoxyuridin-5-yl in Z-form DNA"; Tetrahedron Letters 1999, 40, 2589-2592.
4. Oyoshi, T.; Kawai, K.; Sugiyama, H., "Efficient C2' α-Hydroxylation of deoxyribose in Protein-Induced Z-form DNA."; J. Am. Chem. Soc., 2003, 125, 1526-1531.

DISCLOSURE OF INVENTION

The present invention has been completed under the above circumstance, and an aspect of the present invention is to provide a novel monomer unit, which can stabilize Z-form DNA more effectively, a reagent for integrating the monomer unit to oligonucleotide, and a method for stabilizing the Z-form DNA by using the reagent.

The present invention relates to a guanosine derivative represented by the following general formula (I):

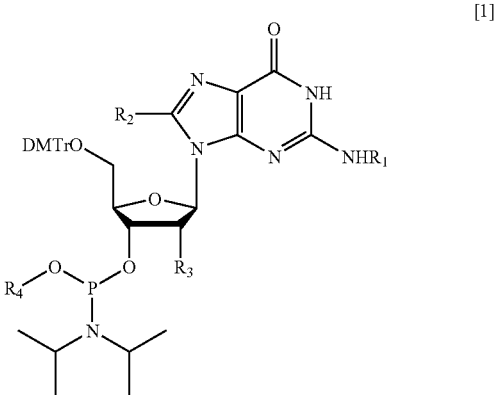

wherein, $R^1$ represents an acyl group, $R^2$ represents a lower alkyl group, $R^3$ represents a tri-substituted silyloxy group or a tetrahydropyranyloxy group, and $R^4$ represents a cyanoethyl group or an allyl group.

Further, the present invention relates to a reagent for stabilizing Z-form DNA comprising said guanosine derivative.

Further, the present invention relates to a method for stabilizing Z-form DNA by using said guanosine derivative.

Further, the present invention relates to a method for integrating guanosine having a lower alkyl group at the position-8 into an oligonucleotide, wherein said guanosine derivative is used.

Further, the present invention relates to an oligonucleotide integrated with guanosine having a lower alkyl group at the position-8.

Namely, as a result of intensive study to solve the above problems, the present inventors have found that 8-methylguanosine, which is guanosine introduced with a methyl group at the position-8, stabilizes Z-form DNA more intensively by several times compared with the abovementioned 8-methyldeoxyguanosine (MeG), and completed the present invention.

BEST MODE FOR CARRYING OUT THE INVENTION

Figure 1:
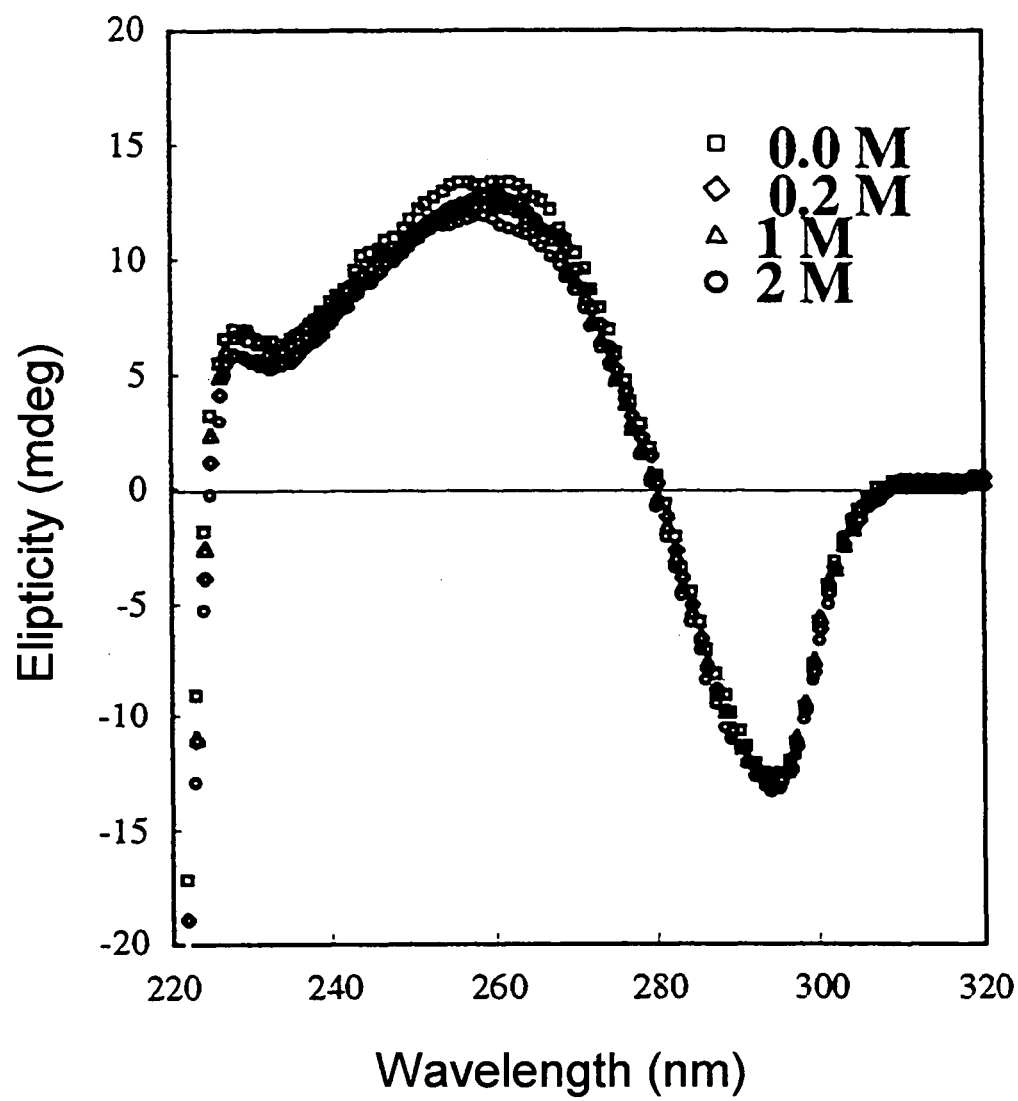
FIG. 1 shows circular dichroism (CD) spectra of three types of oligonucleotide of the present invention obtained in Example 3.
Figure 1:
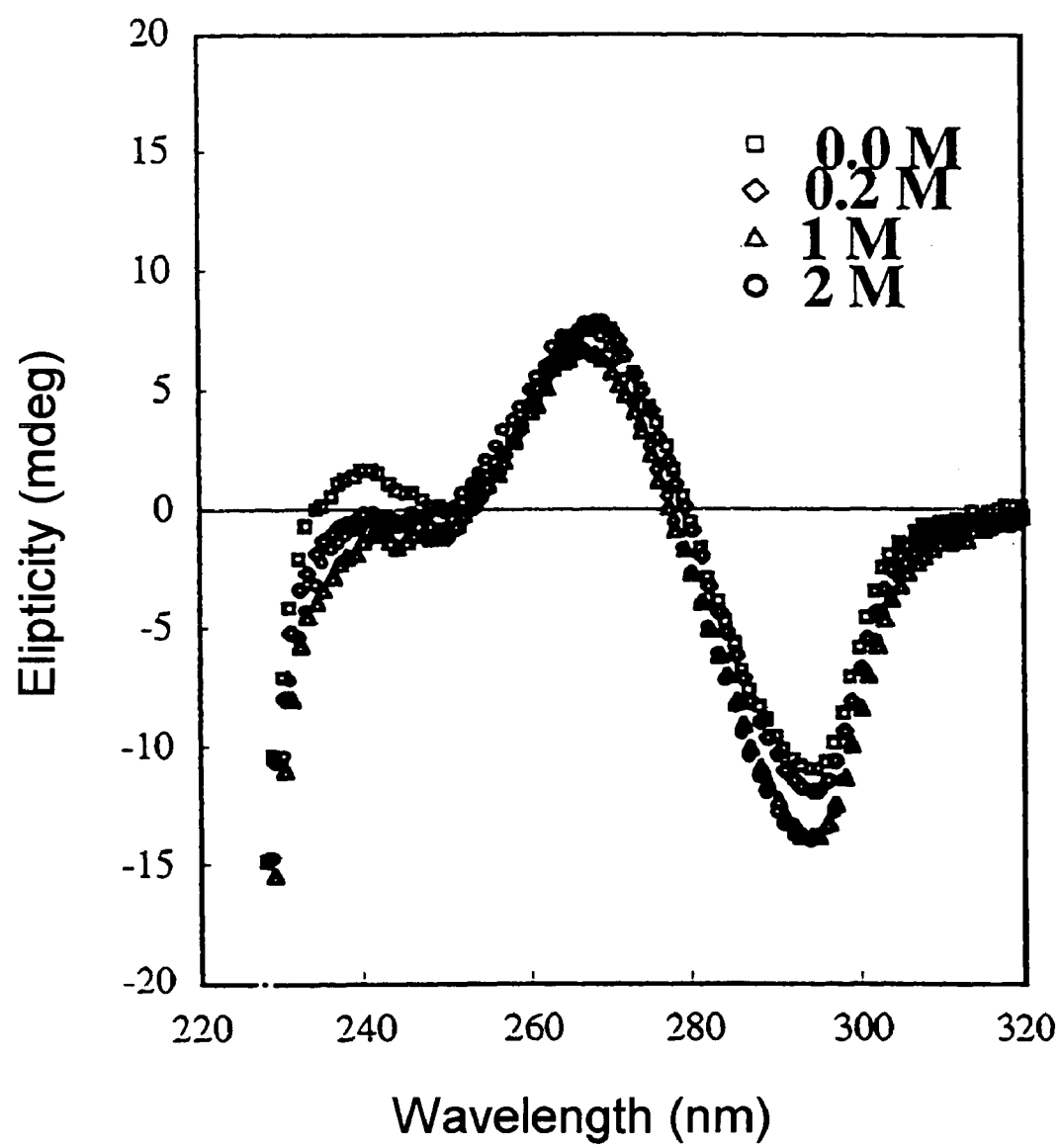
Figure 1:
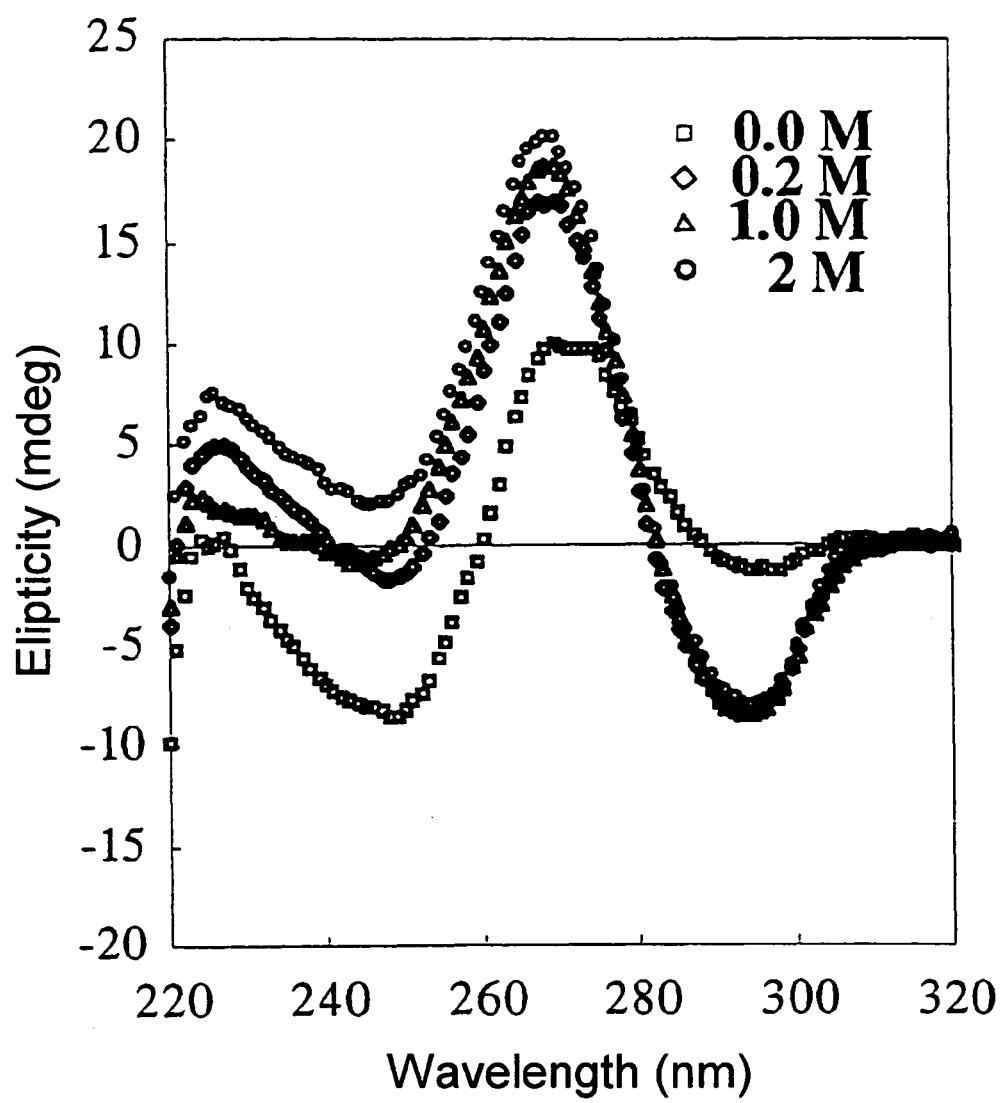

In the general formula [1], the acyl group represented by $R^1$ may be any acyl group so long as it is usually used in this field as a modifying group for amino acid, and preferably includes a bulky acyl group such as an isobutyl group, a benzoyl group and a 4-(t-butyl)benzoyl group.

The lower alkyl group represented by $R^2$ preferably includes a lower alkyl group having 1 to 4 carbon atoms such as methyl, ethyl, n-propyl, isopropyl, n-butyl, s-butyl and t-butyl group, and particularly preferably a methyl group from the viewpoint of easiness in synthesis.

In the above general formula [1], the tri-substituted silyloxy group represented by $R^3$ preferably includes a bulky tri-substituted silyloxy group such as a t-butyldimethylsilyloxy group, a triisopropylsilyloxy group and a triphenylsilyloxy group.

The guanosine derivatives of the present invention represented by the above general formula [1] are quite useful as a monomer unit for stabilizing Z-form DNA.

Namely, the Z-form DNA can be intensively stabilized using the guanosine derivatives of the present invention represented by the above general formula [1].

In more detail, by using the guanosine derivatives of the present invention, Z-form DNA can be stabilized by integrating guanosine having a lower alkyl group at the position-8 in DNA by means of DNA solid-phase synthesis.

In this connection, various oligonucleotides, to which 8-methylguanosine was integrated by using the guanosine derivative of the present invention represented by the general formula [1], wherein $R^1$ was an isobutyryl group, $R^2$ was a methyl group, $R^3$ was a t-butyldimethylsilyloxy group and $R^4$ was a cyanoethyl group, extremely lowered midpoint of the B-Z transition as compared with oligonucleotides, to which 8-methyldeoxyguanosine was integrated by the similar procedures. From these results, it has been found that oligonucleotides integrated with the guanosine derivatives of the present invention have a stronger stabilizing effect than those with the deoxyguanosine derivative of the prior art by several to several dozen times.

A process for producing the guanosine derivative of the present invention is illustrated in the following reaction scheme by exemplifying the guanosine derivative of the general formula [1], wherein $R^1$ is an isobutyryl group, $R^2$ is a methyl group, $R^3$ is a t-butyldimethylsilyloxy group and $R^4$ is a cyanoethyl group.

In the above reaction scheme:

process a): reaction with trimethylsilyl chloride, subsequently with isobutyric anhydride in pyridine;

process b): reaction with $H_2SO_4$, $FeSO_4$ and t-butyl hydroperoxide in aqueous medium;

process c): reaction with dimethoxytrityl chloride, triethylamine and 4-dimethyaminopyridine in pyridine;

process d): reaction with imidazole and 2'-t-butylmethylsilyl chloride in dichloromethane; and process e): reaction with N,N-diisopropylamine and 2-cyanoethyl N,N-diisopropylphosphoroamidite in dichloromethane.

For details, refer to Examples described later.

The above process b) is a process for methylation of guanosine at the position-8, in which a method described in Tetrahedron, 30, 2677-2682, 1974 is employed, but the alkylation including the methylation of guanosine at the position-8 can be performed by the following method.

That is, after a hydroxyl group in ribose is protected, for example, with a t-butyldimethylsilyl group, the position-8 of guanosine is subjected to lithiation with lithium diisopropylamine (LDA), subsequently reacted with a proper alkyl halide to selectively introduce an alkyl group. Consequently, in case of introducing other alkyl group, this method can be applied (refer to Chem. Pharm. Bull. 35, 72-79, 1987). Introduction of a methyl group can also be performed by this method.

A method for integrating guanosine having a lower alkyl group at the position-8 into an oligonucleotide by using the

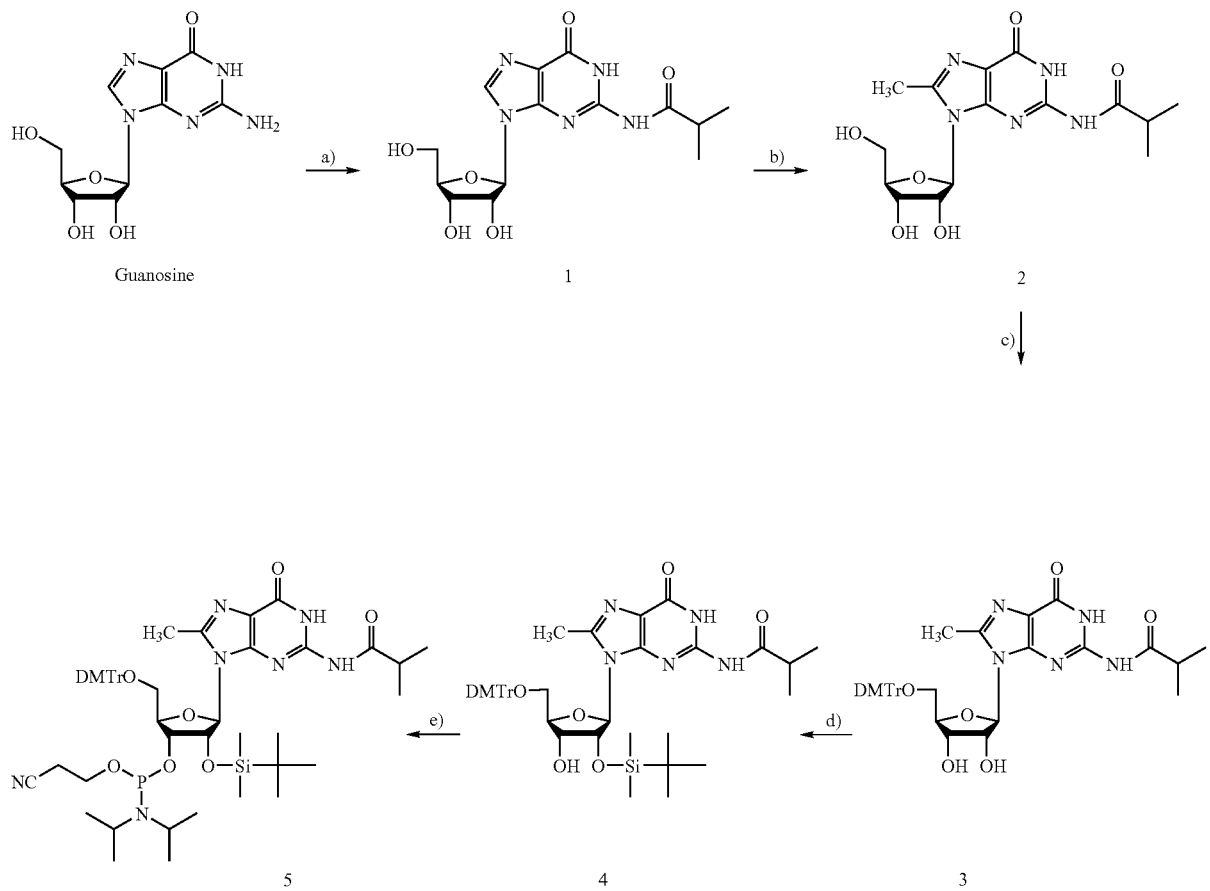

guanosine derivative of the present invention, includes a solid-phase synthesis of DNA oligomer using a commercially available DNA synthesizer. Each operational procedure can be sufficiently performed according to a protocol attached to each of the DNA synthesizers.

The content of the specification of JP Application No. 2003-052815 is incorporated herein in its entirety.

EXAMPLES

The present invention will be explained more specifically by using Examples, however, the present invention should not be construed to be limited by these Examples.

Example 1

Synthesis of 8-methyl-N-isobutyryl-5'-O-dimethoxytrityl-2'-t-butyldimethylsilyl-guanosine-(2-cyanoethyl-N,N-diisopropylphosphoroamidite (Compound 5)(guanosine derivative of the general formula [1], wherein $R^1$ is an isobutyryl group, $R^2$ is a Methyl Group, $R^3$ is a t-butyldimethylsilyloxy group and $R^4$ is a cyanoethyl group)

(1) Synthesis of N-isobutyl-guanosine (Compound 1):

Guanosine (7 g, 25 mmol) was dried three times by evaporation of pyridine and suspended in pyridine (140 ml). Trimethylsilyl chloride (17.5 ml, 125 mmol) was added thereto. After the solution was stirred for 2 hours, isobutyric anhydride 21 ml (125 mmol) was added, and the mixture was stirred for 4 hours at room temperature. After the reaction was completed, the reaction mixture was added with water (35 ml) under ice-cooling, and stirred for further 15 minutes. Then, the reaction mixture was added with 29% aqueous ammonia (35 ml) and stirred for 10 minutes. After the solvent was removed off in vacuo, the residue was extracted with dichloromethane 200 ml, and purified by the silica gel column chromatography (developing solvent: methanol/dichloromethane=2/8) to obtain Compound 1 (3.6 g, yield: 39%).

NMR spectral data of thus obtained compound are shown below.

$^1$H NMR (500 MHz, DMSO-$d_6$) δ: 8.24 (s, 1H, H-8), 5.80 (m, 1H, 1'), 4.42 (m, 1H, 2'), 3.88 (m, 4'), 4.08 (m, 1H, 3'), 3.33 (m, 2H, 5'), 2.77 (m, 1H, isobutyryl CH), 1.12 (d, 6H, J=7 Hz, 2CH$_3$) ppm.

(2) Synthesis of 8-methyl-N-isobutyl-guanosine (Compound 2):

To a solution of $H_2SO_4$ (1N) 160 ml containing the Compound 1 (1 g, 2.6 mmol) obtained in (1) and FeSO$_4$.7H$_2$O (6.7 g, 24.1 mmol), an aqueous solution (100 ml) containing 70% t-butyl hydroperoxide (9.5 mmol) was added dropwise over a period of 5 minutes. After being stirred at 0° C. for 1 hour, the reaction mixture was neutralized with aqueous saturated KOH solution. The supernatant obtained by centrifugation was concentrated in vacuo, and the residue was purified by the silica gel column chromatography (developing solvent: methanol/dichloromethane=1/9) to obtain Compound 2 (0.4 g, yield: 41%).

NMR spectral data of thus obtained compound are shown below.

$^1$H NMR (500 MHz, DMSO-$d_6$) δ: 5.81 (m, 1H, 1'), 4.32 (m, 1H, 2'), 3.86 (m, 4'), 4.12 (m, 1H, 3'), 3.29 (m, 2H, 5'), 2.78 (m, 1H, isobutyryl CH), 2.47 (s, 3H, −8 CH$_3$), 1.11 (d, 6H, J=7 Hz, 2CH$_3$) ppm.

(3) Synthesis of 8-methyl-N-isobutyryl-5'-O— dimethoxytrityl-guanosine (Compound 3):

The Compound 2 (500 mg, 2.4 mmol) obtained in (2) was dried three times by evaporation of pyridine and suspended in pyridine (140 ml). Dimethoxytrityl chloride (DMTrCl, 700 mg, 3.7 mmol), triethylamine (0.3 ml, 2.1 mmol) and 4-dimethylaminopyridine (4.2 mg, 0.035 mmol) were added thereto, and the reaction mixture was stirred at room temperature overnight. After the reaction was completed, the reaction mixture was added with 5% aqueous solution of NaHCO$_3$ (50 ml) under ice-cooling, the reaction mixture was extracted with dichloromethane (60 ml), and the extract was purified by the silica gel column chromatography (developing solvent: methanol/dichloromethane=3/97) to obtain Compound 3 (0.5 g, yield: 60%).

NMR spectral data of thus obtained compound are shown below.

$^1$H NMR (500 MHz, DMSO-$d_6$) δ: 5.81 (m, 1H, 1'), 4.32 (m, 1H, 2'), 3.86 (m, 4'), 4.12 (m, 1H, 3'), 3.29 (m, 2H, 5'), 2.78 (m, 1H, isobutyryl CH), 2.47 (s, 3H, −8 CH$_3$), 1.11 (d, 6H, J=7 Hz, 2CH$_3$) ppm.

(4) Synthesis of 8-methyl-N-isobutyryl-5'-O-dimethoxytrityl-2'-t-butyldimethylsilyl-guanosine (Compound 4):

To a dichloromethane solution (25 ml) containing the Compound 3 (1 g, 1.4 mmol) obtained in (3) and imidazole (238 g, 3.5 mmol), 2'-t-butyldimethylsilyl chloride (252 mg) was added, and the mixture was stirred at 20° C. for 16 hours.

After the reaction was completed, 10% aqueous solution of NaHCO$_3$ (30 ml) was added to the reaction mixture. The reaction mixture was extracted with dichloromethane (40 ml), and the extract was purified by the silica gel column chromatography (developing solvent: hexane/ethyl acetate=5/1) to obtain Compound 4 (0.3 g, yield: 30%).

NMR spectral data of thus obtained compound are shown below. $^1$H NMR (500 MHz, DMSO-$d_6$) δ: 7.20-7.39 (m, 9H, ph), 6.89 (d, 4H, J=8.5 Hz, ph), 4.96 (m, 1H, 1'), 4.16 (m, 1H, 3'), 3.74 (s, 6H, 2CH$_3$), 3.18 (m, 2H, 5'), 3.02 (m, 1H, 6'), 2.77 (m, 1H, isobutyryl CH), 2.14 (m, 1H, 2'), 2.05 (m, 2H, 2" and 4'), 1.88 (s, 3H, −8 CH$_3$), 1.62 (m, 1H, 6"), 1.10 (d, 6H, J=7 Hz, 2CH$_3$) ppm.

(5) Synthesis of 8-methyl-N-isobutyryl-5'-O-dimethoxytrityl-2'-t-butyldimethylsilyl-guanosine-(2-cyanoethyl-N,N-diisopropylphosphroamidite (Compound 5):

The Compound 4 (300 ml, 0.4 mmol) obtained in (4) was sealed in a rubber-sealed bottle. After sealing the bottle, dry acetonitrile (3 ml) was added thereto, and inside of the bottle was evacuated by reduced pressure through a needle to evaporate acetonitrile and remove water by azeotrope. Dry dichloromethane (3 ml) was injected by a syringe, and dry N,N-diisopropylamine (0.45 ml, 0.6 mmol) and 2-cyanoethyl-N,N-diisopropylphosphoroamidite (0.25 ml, 1 mmol) were added thereto. The reaction mixture was stirred at room temperature overnight. After 10% aqueous NaHCO$_3$ solution (10 ml) was added, the reaction mixture was extracted with dichloromethane (20 ml), and the organic layer was dried over Na$_2$SO$_4$. The extract was purified by the silica gel column chromatography (developing solvent: hexane/acetone/triethylamine=49/49/2) to obtain Compound 5 (240 mg yield: 60%).

Spectral data of thus obtained compound are shown below.
ESIMS (m/e) as $C_{52}H_{75}N_{709}PSi$: Calculated: (M+H) 1000.5. Observed: 1000.8. (Measured by using PE SCIEX API 165)

Example 2

Solid Phase Syntheses of DNA Oligomers

The compound 5 (200 ml, 0.2 mmol) obtained in Example 1 was sealed in a rubber-sealed bottle. Dry acetonitrile (2 ml) was added thereto and evaporated in vacuo. The residue was dissolved by adding dry acetonitrile (0.3 ml), and the solution was supplied to the OLIGO 1000 DNA synthesizer (Beckman Inc.), then oligonucleotide d (CGCMerGCG), d (CMerGCACMerGCG) and d (CMerGCATMerGTG) were synthesized according to the protocol attached to the DNA synthesizer.

Compositions and concentrations of the synthesized oligonucleotides were confirmed by enzymatic hydrolysis to mononucleosides.

In the sequences of the above oligonucleotides, MerG represents 8-methylguanosine.

Example 3

Circular Dichroism Experiments

Circular dichroism spectra of three types of oligonucleotides obtained in Example 2 were analyzed using the circular dichroism spectrophotometer (AVIV MODEL 62 DS/202 CD spectrophotometer, AVIV Biomedical Inc.). CD (circular dichroism) spectra of the oligonucleotides (concentration: 0.15 mM base conc., 5 mM sodium cacodylate buffer, pH 7.0) were measured by using a cell, 1 cm in length, in various concentrations of NaCl. Results are shown in FIG. 1.

FIG. 1 (a) shows CD spectra of oligonucleotide 5'-CGC-MerGCG-3'; FIG. 1 (b) shows CD spectra of oligonucleotide 5'-CMerGCACMerGCG-3'; and FIG. 1 (c) shows CD spectra of oligonucleotide 5'-CMerGCATMerGTG-3'.

Further, a NaCl concentration at the midpoint of B-Z transition of each oligonucleotide was obtained by measuring CD spectra with the concentration of NaCl varied. Results are shown in Table 1. For comparison, an oligonucleotide, to which 8-methyldeoxyguanosine (MeG) is introduced in place of 8-methylguanosine (MerG), was measured similarly, and the results are also shown in Table 1.

In Table 1, MeG represents 8-methyldeoxyguanosine and MerG represents 8-methylguanosine.

TABLE 1

| Experiment 1 | d(CGCGCG) | 2.6 M |
| Experiment 2 | d(CGCMeGCG) | 30 mM |
| Experiment 3 | d(CGCMerGCG) | <5 mM |
| Experiment 4 | d(CGCGTGCG)/d(CMeGCACMeGCG) | 800 mM |
| Experiment 5 | d(CGCGTGCG)/d(CMerGCACMerGCG) | 50 mM |
| Experiment 6 | d(CMeGCATMeGTG)/d(GCGTACAC) | 2450 mM |
| Experiment 7 | d(CMerGCATMerGTG)/d(GCGTACAC) | 200 mM |

As apparent from Table 1, it can be understood that the integration of 8-methylguanosine into various oligonucleotides results in significant lowering of the midpoint in any case, showing stabilization of Z-form DNA even in very low concentration of salt. The reason may be that when a methyl group is introduced in guanosine at the position-8, the base thereof has a tendency to adopt a syn orientation, and the introduction of a hydroxyl group at the position-2' results in an increase of hydrophilicity, and puckering of sugar is further stabilized by adopting a C3'-endo conformation.

INDUSTRIAL APPLICABILITY

The present invention provides 8-methylguanosine, which is a novel monomer unit capable of stabilizing Z-form DNA more effectively, a guanosine derivative represented by the general formula [1], which is a reagent for integrating the monomer unit into an oligonucleotide, and a method for stabilizing Z-form DNA by using the reagent. Since 8-methylguanosine of the present invention, which is a compound prepared by introducing a methyl group in guanosine at the position-8, can stabilize Z-form DNA more potently by several times as compared with the conventionally known 8-methyldeoxyguanosine (MeG), it can be predictable to be an excellent tool for studying the Z-form DNA.

The invention claimed is:

1. A method for stabilizing Z-form DNA, comprising synthesizing DNA with a guanosine derivative represented by general formula [1]:

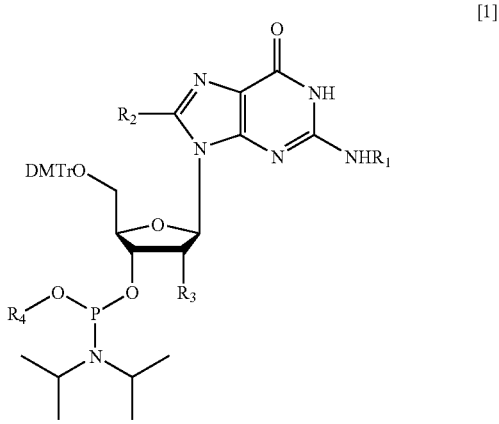

[1]

wherein, $R^1$ represents an acyl group, $R^2$ represents a lower alkyl group, $R^3$ represents a protected hydroxyl group, $R^4$ represents a cyanoethyl group or an allyl group, and DMTr represents a dimethoxytrityl group.

2. The method of claim 1, wherein the DNA is synthesized using solid-phase synthesis.

* * * * *